(12) United States Patent
Mak (10) Patent No.: US 8,377,403 B2
(45) Date of Patent: Feb. 19, 2013

(54) CONFIGURATIONS AND METHODS FOR REMOVAL OF MERCAPTANS FROM FEED GASES

(75) Inventor: John Mak, Santa Ana, CA (US)

(73) Assignee: Fluor Technologies Corporation, Aliso Viejo, CA (US)

( * ) Notice: Subject to any disclaimer, the term of this patent is extended or adjusted under 35 U.S.C. 154(b) by 793 days.

(21) Appl. No.: 12/375,337

(22) PCT Filed: Jul. 30, 2007

(86) PCT No.: PCT/US2007/017054
§ 371 (c)(1),
(2), (4) Date: Oct. 19, 2009

(87) PCT Pub. No.: WO2008/020994
PCT Pub. Date: Feb. 21, 2008

(65) Prior Publication Data
US 2011/0237856 A1    Sep. 29, 2011

Related U.S. Application Data

(60) Provisional application No. 60/821,924, filed on Aug. 9, 2006.

(51) Int. Cl.
*B01D 47/02* (2006.01)
*B01D 53/48* (2006.01)
*B01D 53/52* (2006.01)
*B01D 53/14* (2006.01)
*B01D 53/18* (2006.01)

(52) U.S. Cl. ........... 423/242.1; 95/209; 95/229; 95/235; 96/243

(58) Field of Classification Search .................. 95/209, 95/229, 235; 96/243; 423/242.1
See application file for complete search history.

(56) References Cited

U.S. PATENT DOCUMENTS

| 4,025,315 A | 5/1977 | Mazelli |
| 4,100,256 A | 7/1978 | Bozzelli et al. |
| 4,524,050 A | 6/1985 | Chen et al. |
| 5,890,378 A | 4/1999 | Rambo et al. |
| 6,837,070 B2 | 1/2005 | Mak |

*Primary Examiner* — Randy Boyer
(74) *Attorney, Agent, or Firm* — Fish & Associates, PC (57) ABSTRACT

Contemplated configurations and methods employ COS hydrolysis and a downstream H2S removal unit to produce a treated feed gas that is then further desulfurized in an absorber using two lean oil fluids. The so produced mercaptan enriched hydrocarbon fluid is fed to a distillation column that produces a light overhead vapor that is preferably combined with the treated feed gas and a sulfur rich bottom product that is in most cases preferably directly fed to a hydrocarbon processing unit comprising a hydrotreater. In further especially preferred aspects, the hydrocarbon processing unit produces at least one and more typically both of the two lean oil fluids, and the treated gas is optionally further processed to produce clean fuel gas in a hydrotreater for olefinic saturation and sulfur conversion using a lean oil recycle for reactor temperature control.

20 Claims, 6 Drawing Sheets

CONFIGURATIONS AND METHODS FOR REMOVAL OF MERCAPTANS FROM FEED GASES

This application claims priority to our U.S. provisional patent application with the Ser. No. 60/821,924, which was filed Aug. 9, 2006.

FIELD OF THE INVENTION

The field of the invention is gas processing and treating, and especially gas processing and treating to remove sulfur-containing compounds from natural gas and refinery fuel gas and saturation of olefinic hydrocarbons.

BACKGROUND OF THE INVENTION

It is well known in the art to remove acid gas ($H_2S$ and $CO_2$) and other contaminants from gas streams using more or less selective solvents. However, as many gas streams also contain substantial quantities of olefins, heavy hydrocarbons, sulfur dioxide, and especially mercaptans and other organic sulfurous compounds (e.g. methyl mercaptan, ethyl mercaptan, butyl mercaptan, carbonyl sulfide, dimethyl disulfide, carbon disulfide, propanethiol, and thiophene), undesirable side reactions with the solvent or other treating medium (e.g., fixed bed catalyst) often render the solvent/treating and reactor media ineffective and necessitate plant shutdown. To avoid difficulties associated with such side reactions, pre- and post treatment units can be implemented to render a gas stream more suitable processing and/or for emission into the environment.

Figure 1:
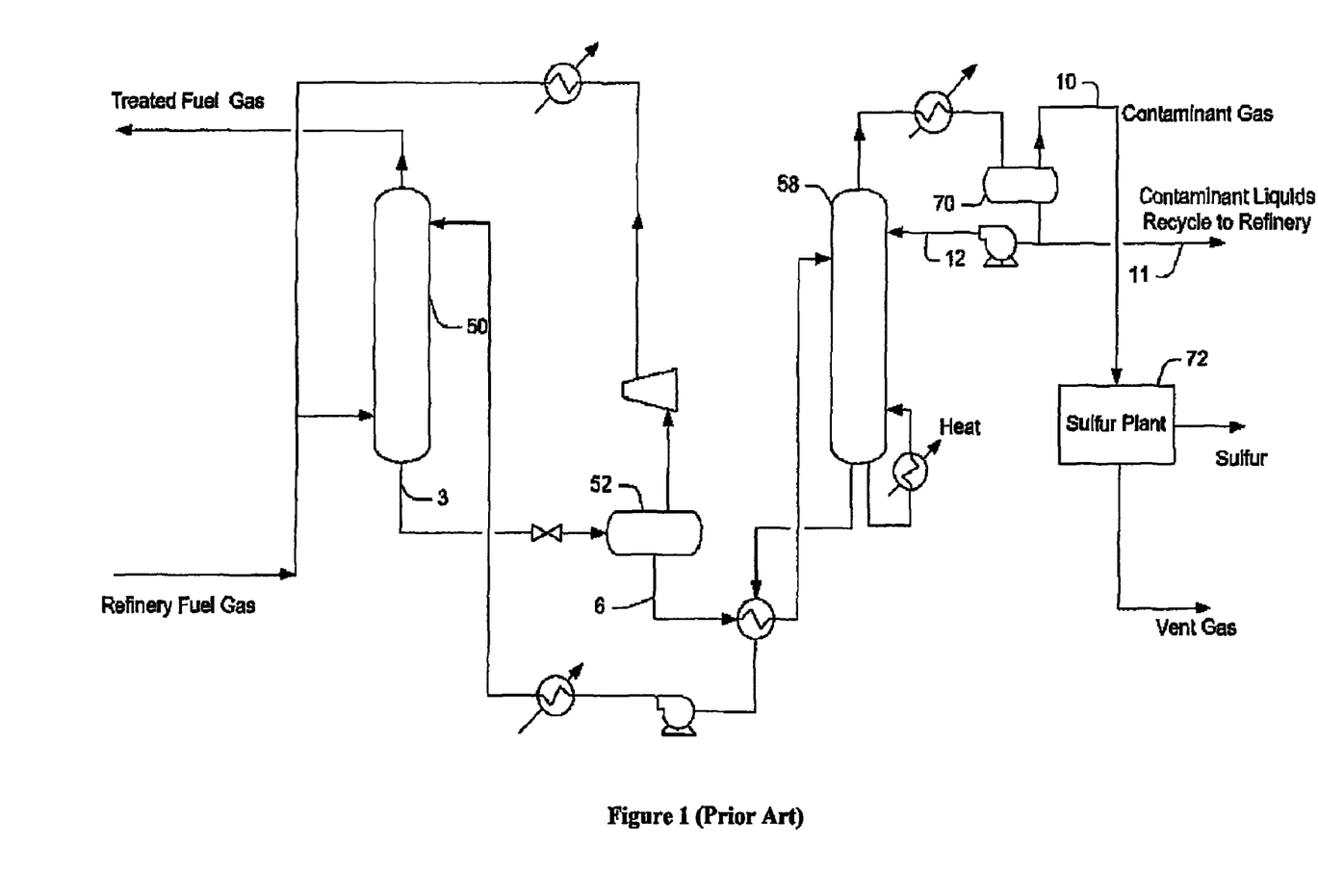
FIG. 1 is an exemplary schematic of a known gas treatment plant.

An exemplary known gas treatment configuration that employs a solvent is depicted in Prior Art FIG. 1 in which the acid gases are absorbed in an absorber 50 that forms a rich solvent 3. The rich solvent 3 is then flashed in a flash drum 52, with the vapors being recycled to the absorber 50 while the liquid 6 is routed to the regenerator 58. Here, the acid gases are removed from the solvent to form the lean solvent that is cross exchanged with the rich solvent 6 before entering again the absorber 50. The so absorbed acid gases and other sulfurous compounds are stripped in the regenerator and separated in an overhead separator 70 to form a reflux 12 for the regenerator, a contaminant vapor 10, and a contaminant liquid 11. Contaminant gases 10 are typically further processed in a Claus plant 72, while the contaminant liquids 11 are frequently recycled to a refinery for disposal. Most commonly, the solvent is a physical solvent or amine (e.g. propylene carbonate, tributyl phosphate, methyl pyrolidone, and other various polyethylene glycol dialkyl ethers, formulated tertiary amine or other amines) that can be used to at least some degree in the removal of mercaptans and heavy hydrocarbons.

While such processes generally operate satisfactorily under certain circumstances, several problems nevertheless remain. Among other things, amine solvents are often ineffective in removal of mercaptans and organic sulfur. Physical solvents can typically absorb these contaminants. However, such solvents tend to co-absorb hydrocarbons and thus produce laden liquid and vapor waste streams that create emission problems downstream. Additionally, residual olefinic hydrocarbons in the treated gas may further react with fixed bed absorbents or hydrotreating catalysts forming gums rendering such processes unsafe and inoperable. Still further, high levels of heavier hydrocarbons and mercaptans in the acid gases often create conversion problems in a downstream sulfur plant. For example, for complete destruction of mercaptans and other organic sulfurs contaminants, the Claus reaction furnace must be operated at a high flame temperature, which will significantly reduce the life of the sulfur plant. Moreover, even with higher flame temperatures, destruction of the heavier mercaptans is often difficult and incomplete, which results in fouling of the reaction catalysts and ultimately plant shutdown To circumvent at least some of the problems associated with inadequate contaminant removal, various pre- and post treatment methods have been employed. Unfortunately, most of such methods tend to be relatively ineffective, inefficient and costly, and where contaminants are removed by a fixed bed absorbent process, they may further pose a disposal problem for the spent absorbent. Therefore, various problems associated with operating efficiency, effluents, emissions, and product qualities, and particularly in the downstream sulfur plant, tail gas unit and fuel gas conditioning unit still remain. For example, acid gas produced from such treating processes is generally poor in quality (e.g., comprising significant quantity of contaminants, and/or a relatively large quantity of co-absorbed $CO_2$ and hydrocarbons), and the treated gas typically contains significant quantities of environmentally undesirable olefinic hydrocarbons, which often requires additional processing and energy consumption, thereby increasing the capital and operating costs.

In still other known processes, especially with hydrotreater processing high olefinic hydrocarbons (ethylene, propylene, propyldienes, butenes and butadienes and heavy olefins), the reliability and available of such units are typically very low due to fouling from the heavier components ($C_6^+$) in the feed gases. The residual olefinic hydrocarbons in the treated gas from these processes will result in excessive NOx formation in the burners and power generation equipment that may necessitate shutdown of the facility. Therefore, while various gas processing treatments and configurations are known in the art, all or almost all of them suffer from one or more disadvantages, and especially where the feed gas comprises relatively high levels of acid gases, olefinic hydrocarbons, mercaptans and organic sulfurs contaminants.

SUMMARY OF THE INVENTION

The present invention is directed to plant configurations and methods in which a feed gas is subjected to COS hydrolysis and $H_2S$ removal to form a treated feed gas that is then further desulfurized in an absorber using two lean hydrocarbon fluids to produce a cleaned feed gas and a mercaptan enriched hydrocarbon fluid. A distillation unit then separates a light overhead vapor from a sulfur rich bottom product that is fed to a hydrocarbon processing unit that comprises a hydrotreater to form a sulfur-containing product (e.g., for delivery to a Claus plant) and one, and more typically both of the two lean hydrocarbon fluids. Most preferably, the treated gas is further processed in a hydrotreating unit specifically configured to process the high olefinic feed gases.

In one especially preferred aspect of the inventive subject matter, a gas treatment plant includes a COS hydrolysis unit that hydrolyzes COS in a mercaptan-containing feed gas to form a treated feed gas. An absorber is coupled to the COS hydrolysis unit and receives via first and second conduits first and second lean hydrocarbon fluids, respectively, and the treated feed gas is then contacted in the absorber with the first and a second lean hydrocarbon fluids to produce a mercaptan enriched hydrocarbon fluid and a desulfurized product gas. A distillation column is fluidly coupled to the absorber, receives the mercaptan enriched hydrocarbon fluid, and produces a light overhead vapor and a sulfur rich bottom product that is depleted of the $C_3/C_4$ lighter hydrocarbons. Contemplated plants will further include a hydrocarbon processing unit comprising a hydrotreater, wherein the hydrocarbon processing unit is fluidly coupled to the distillation column to receive the sulfur rich bottom product and to produce a sulfur-containing product and the first and/or second lean hydrocarbon fluid.

In another aspect of the especially preferred configuration, the treated gas from the gas treatment plant is further processed in a hydrotreating unit that saturates the olefinic hydrocarbons to paraffinic hydrocarbons producing a clean fuel gas to the power plants and steam boilers. In preferred configurations, a lean oil recycled from the reactor outlet separator is mixed with the reactor feed that cools the hydrotreater reactor via evaporation thus controlling the hydrotreater reaction temperature and minimizing formation of undesirable by-products (e.g., gums and carbon deposits)

Viewed from a different perspective, a method of removing sulfur compounds from a feed gas therefore includes a step of hydrolyzing COS in a sulfur and mercaptan-containing feed gas to form a treated feed gas. In another step, sulfur species are absorbed from the treated feed gas in an absorber using a first and a second lean hydrocarbon fluid to thereby produce a mercaptan enriched fluid and a desulfurized product gas, and in yet another step, the mercaptan enriched fluid is separated in a distillation column to produce a light overhead vapor and a sulfur rich bottom product. The sulfur rich bottom product is then processed in a hydrocarbon processing unit that has a hydrotreater to produce a sulfur-containing product and at least one of the first and second lean hydrocarbon fluid while the treated gas is further processed in a hydrotreating unit specifically design to convert the residual mercaptan contaminants and saturate the olefinic hydrocarbons.

Most preferably, $H_2S$ is removed in an $H_2S$ removal unit prior to feeding the treated feed gas into the absorber, and the light overhead product of the distillation column is mixed with the treated feed gas. It is further particularly preferred that the hydrocarbon processing unit produces the first and second lean hydrocarbon fluids, and that respective coolers cool the first and second lean hydrocarbon fluids prior to feeding into the absorber.

Where desired, a second absorber may be coupled upstream to the absorber, wherein the second absorber receives the treated feed gas and produces an overhead gas and a second mercaptan enriched hydrocarbon fluid, and wherein the second absorber provides the overhead gas to the first absorber. In such plants, the first conduit preferably provides the first lean hydrocarbon fluid to the overhead gas prior to entering the first absorber. Alternatively, an absorber overhead condenser and reflux drum may be implemented to produce a reflux to the absorber as the first lean hydrocarbon fluid via the first conduit, and the desulfurized product gas is mixed with the second lean hydrocarbon fluid via the second conduit in a location upstream of the reflux drum. In such plant configurations, it is preferred that the overhead condenser cools the first and second lean hydrocarbon fluids.

Various objects, features, aspects and advantages of the present invention will become more apparent from the following detailed description of preferred embodiments of the invention, along with the accompanying drawing.

BRIEF DESCRIPTION OF THE DRAWING

Prior Art

DETAILED DESCRIPTION

The inventor discovered that gas streams, and especially gas streams containing COS, $H_2S$, $CO_2$, mercaptans, olefins, and heavy hydrocarbons can be treated in a process where the COS is first hydrolyzed to $H_2S$, and where the $H_2S$ is then removed from the gas stream in a conventional $H_2S$ removal unit. The remaining sulfur-containing compounds in the gas stream are then absorbed by preferably two cooled lean oil ($C_6^+$ hydrocarbons) streams with low to ultra-low sulfur content to produce a sulfur-rich solvent and a desulfurized gas stream.

Most preferably, the second lean oil is substantially sulfur free (e.g., equal or less than 100 ppmw) and is a lean oil suitable for complex sulfur absorption that is heavier than the first lean oil that also has a relatively low sulfur content (typically less than 0.1 wt %). Thus, the desulfurized gas stream can be effectively purified to a desirable level. Co-absorbed light hydrocarbons ($C_3/C_4^+$ fractions) are subsequently removed from the sulfur-rich solvent in a distillation column and fed back to the absorber, while the treated the sulfur-rich and $C_3/C_4^+$ fractions depleted solvent is refined in a hydrocarbon processing unit that includes a hydrotreater to desulfurize the sulfur-rich solvent and thereby produce at least one, and more preferably both of the lean oil streams. Alternatively, a single lean oil stream may be employed. In such configurations, a catalytic oxidation stage and second distillation column is typically needed to treat the rich solvent stream prior to feeding the stream to the hydrocarbon processing/hydrotreater unit for regeneration of the lean oil.

Regardless of the number of lean oil streams employed, it is generally preferred that the lean oil or lean oil streams are regenerated in a refinery unit that is configured to process hydrocarbon feeds (from the gas plant such as debutanizer bottoms in the refinery units) to thereby produce the lean oil stream(s). Moreover, it is generally preferred that the hydrocarbon processing unit includes a hydrotreater unit in which mercaptans and other sulfur containing compounds are catalytically converted to the respective desulfurized hydrocarbon products and a $H_2S$ containing stream that is then routed to an amine unit or Claus unit.

It should be appreciated that suitable feed gas compositions may vary considerably, and that feed gases contemplated herein therefore include natural gas at various pressures, synthesis gas, landfill waste gases, and various refinery off-gases. However, in especially preferred aspects, the feed gas is a low pressure, low quality refinery gas with a composition of about 0.1 to 1% $CO_2$, 20 to 60% C1, 0.001 to 1% $H_2S$, 2 to 20% H2, 2 to 10% C2-C5, 0.05 to 5% C6-C7, 0.01 to 0.5% C8-C9$^+$, 5 to 10% olefinic hydrocarbons, 0.001 to 1% mercaptans, organic disulfides, thiophenes, carbonyl sulfides and sulfur oxide contaminants, with the balance being inerts (e.g., O2 and N2). One exemplary feed gas composition and compositional analysis of selected streams in a configuration (as depicted in FIG. 2) according to the inventive subject matter is depicted in Table 1 below.

|  | Refinery Gas | Sour LPG | Naphtha | C6+ Product | Treated Gas |
|---|---|---|---|---|---|
| Stream No. | 1 | 19 | 8 | 18 | 12 |
| Hydrogen | 0.111032 | 0.000020 | — | — | 0.078785 |
| Nitrogen | 0.000163 | 0.037378 | — | 0.000000 | 0.011724 |
| O2 | 0.085174 | 0.226166 | — | 0.000000 | 0.130676 |
| CO2 | 0.007465 | 0.000374 | — | 0.000000 | 0.005413 |
| CO2 | 0.001059 | — | — | 0.000000 | 0.000751 |
| C1 | 0.524923 | 0.009095 | — | 0.000000 | 0.375265 |
| C2 | 0.203990 | 0.022187 | — | 0.000000 | 0.151624 |
| C3 | 0.010486 | 0.156507 | — | 0.000000 | 0.055925 |
| iC4 | 0.006083 | 0.512797 | — | 0.000643 | 0.159480 |
| NC4 | 0.007358 | 0.031281 | — | 0.214714 | 0.006126 |
| iC5 | 0.000076 | 0.000001 | — | 0.461286 | 0.000003 |
| nC5 | 0.004575 | — | — | 0.000000 | 0.003246 |
| C6+ | 0.040000 | 0.000000 | — | 0.323357 | 0.021000 |
| H2S | 0.000007 | 0.004000 | — | — | 0.000005 |
| COS | 0.000221 | 0.000004 | — | — | 0.000007 |
| M-Mercaptan | 0.000220 | 0.000114 | — | — | 0.000000 |
| E-Mercaptan | 0.000271 | 0.000077 | — | — | 0.000000 |
| Thiophenes | 0.000546 | 0.000002 | — | — | 0.000000 |
| lb/hr | 34,104 | 33,971 | 83,092 | 2,051 | 65,856 |
| BPD | 6,334 | 4,133 | 7,762 | 266 | 10,188 |

Figure 2:
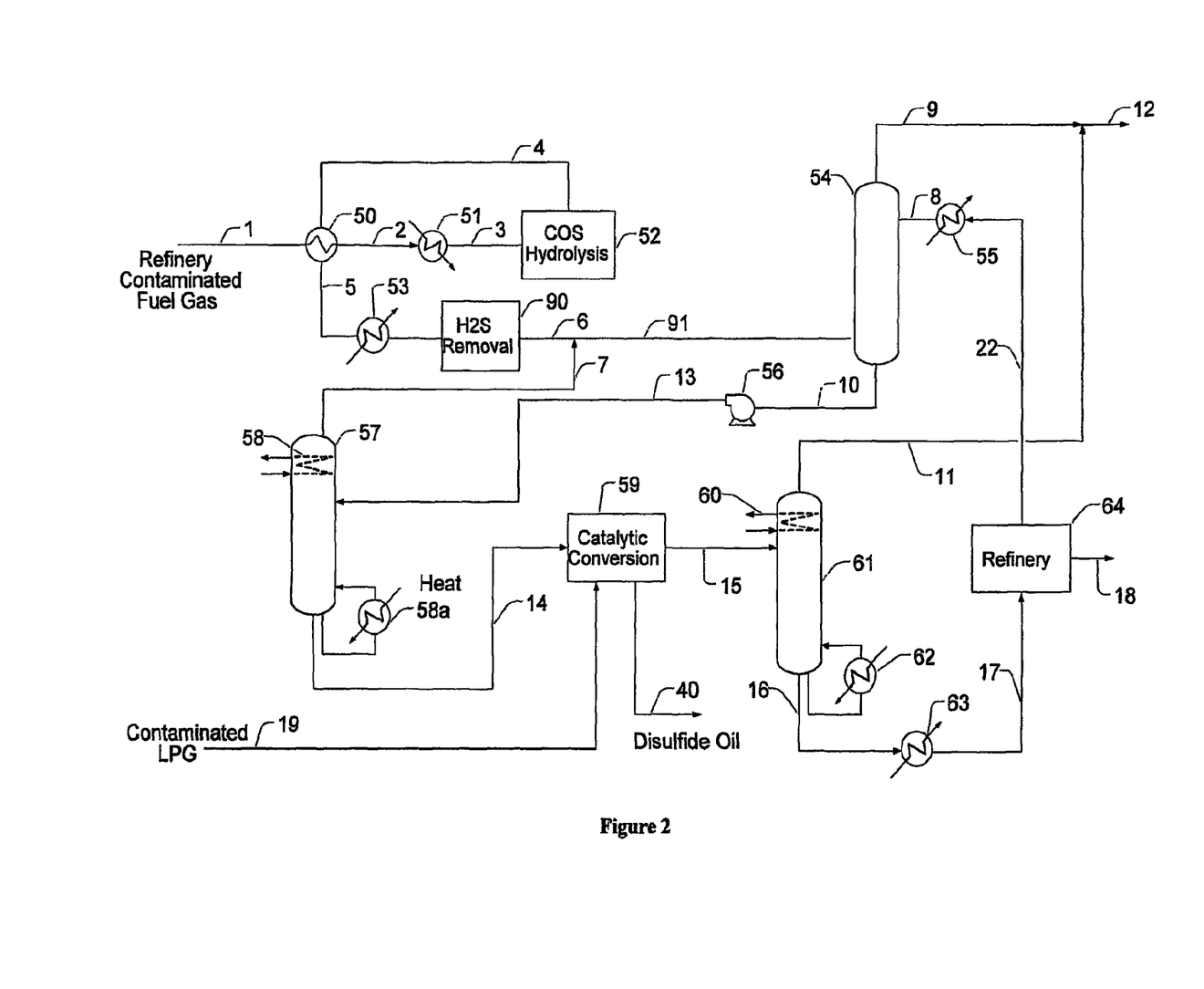
FIG. 2 is an exemplary schematic of a gas treatment plant according to the inventive subject matter.

In one exemplary configuration using a single lean oil stream as depicted in FIG. 2, contaminated refinery feed gas stream 1, at about 100° F. and about 100 psig to about 200 psig, is heated in an exchanger 50 to about 200° F. to about 350° F. forming stream 2, typically using the waste heat from the COS hydrolysis effluent stream 4. As used herein, the term "about" in conjunction with a numeral refers to a range of that numeral starting from 10% below the absolute of the numeral to 20% above the absolute of the numeral, inclusive. For example, the term "about −100° F." refers to a range of −80° F. to −120° F., and the term "about 1000 psig" refers to a range of 800 psig to 1200 psig.

Stream 2 is further heated (e.g., with steam or hot oil) to about 350° F. in exchanger 51 forming stream 3, which is fed to the COS hydrolysis unit 52, where the COS in the feed gas is converted to $H_2S$ via hydrolysis following the reaction $COS+H_2O \leftrightarrow H_2S+CO_2$. The hydrolysis reaction is an exothermic reaction and in the presence of a low level of $H_2S$ in stream 3, at least over about 95% of the COS content is converted. The so COS depleted gas stream 4 is heat exchanged with the feed gas to about 150° F., forming stream 5 and is further cooled in exchanger 53 to about 90° F. with air cooler or cooling water. The $H_2S$ in cooled stream 5 is removed in a $H_2S$ removal unit 90 (e.g., amine unit or ZnO-based removal unit), producing an $H_2S$ free stream 6 that is combined with stream 7 from distillation column 57, forming stream 91 which is fed to a lower section of absorber 54.

Stream 91 is contacted by single lean oil stream 22, preferably a sulfur depleted (with less than 0.1 wt % sulfur content) hydrocarbon lean oil, in absorber 54 to selectively absorb the mercaptans and organic sulfur contaminants. Most preferably, the lean oil comprises a hydrocarbon lean oil (e.g. naphtha characterized by API Gravity ranging from 45 to 95, and RVP (Reid Vapor Pressure) of 2 to 12.0 psia) to selectively absorb the complex sulfur contaminants (e.g., mercaptans and organic sulfur). Therefore, suitable lean oil may include raw un-hydrotreated naphtha and hydrotreated naphtha, or diesel hydrocarbons that have affinity for complex sulfur contaminants over other compounds, including oxygen, CO, and/or $CO_2$. For example, typical lean oils include naphtha or diesel from a refinery or hydrocarbon processing unit and is characterized by API Gravity ranging from 45 to 95, and RVP (Reid Vapor Pressure) of 2 to 11.0 psia. To further enhance the absorption efficiency, the hydrocarbon oil stream 22 is preferably chilled in exchanger 55 forming stream 8 at about 50° F. to about 90° F., and in most cases cooling water or an external refrigeration unit (e.g., using propane, or an absorption refrigeration unit) is used in exchanger 55. It should be appreciated that lower temperatures will not only reduce the lean oil consumption but also reduce the downstream fractionation duties. The lower chilling temperature is typically limited to the hydrate temperature of the gas in the absorber. For this reason, the chilled temperature is maintained at about 60° F. to about 70° F., or at above the hydrate temperature of the gas in the absorber 54. Alternatively, water can be removed as appropriate.

The absorber 54 produces a bottom liquid stream 10, now enriched in mercaptans and organic sulfurs, that is pumped by pump 56 as stream 13 to distillation column 57 operating at about 150 to 250 psig. The distillation column 57 is preferably configured and operated to produce a bottom liquid 14 with a low ethane concentration (e.g., reboiler 58a is operated to maintain temperature at about 300° F. to about 400° F.). Cooling coil 58 is preferably integrated in the column overhead to provide reflux for rectifying the complex sulfur and heavier components. Optionally, the cooling coil can also be installed external to the column complete with reflux drum and pumps (not shown), and can also be chilled with refrigeration. Thus, the distillation column 57 produces an overhead vapor stream 7 that is depleted in mercaptans and organic sulfur, and that is recycled back to the front section of the plant. It should be especially appreciated that by controlling the column at optimum temperature and pressure, the contaminant depleted lighter vapor component is recycled back to the absorber (without gas compression), while producing a contaminant enriched bottom liquid stream 14. Viewed from a different perspective, the distillation column is typically operated under conditions effective to separate at least part of the lighter hydrocarbons (e.g., propane and lighter, typically excluding the first and second lean oils) as an overhead vapor, which is preferably recycled back to the absorber.

Stream 14 is then processed in a catalytic conversion unit 59, which involves catalytic oxidation of mercaptans to disulfides in the presence of oxygen and caustic (NaOH, or other base as suitable). This process is typically used to treat hydrocarbon feeds (e.g., LPG, heavy straight-run gasolines, visbroken and coker derived naphthas, kerosenes, and diesels), and depending on the particular configuration, feed, pre-, and post-treatment sections may also be necessary. The so formed disulfides oil 40 may be separated in the catalytic unit and recycled back to the hydrotreater unit in the refinery as appropriate (not shown). Catalytic conversion unit 59 (sweetening unit) may also be used to process a contaminated LPG stream 19 (where available or desirable) for production of a mercaptan free hydrocarbon liquid that is further processed in downstream distillation column 61. It should be noted that the disulfides formed in such catalytic units can be separated from the remaining hydrocarbons as mercaptans that can be properly disposed or further converted by recycling to the hydrotreater. The catalytic oxidation unit therefore generates a mercaptan-free hydrocarbon liquid, which is then processed in a second distillation column that produces a sulfur free overhead vapor that is combined with the treated gas from the first absorber forming the treated refinery gas and an organic sulfur-rich lean oil that is recycled back to the refinery. Thus, it should be appreciated that the contemplated configuration produces a treated gas with total sulfur content typically less than about 40 ppmv, and most typically less than about 20 ppmv, while the bottom liquid of the distillation column may be further fractionated in a refinery into a saleable $C_6^+$ hydrocarbon liquid.

Second distillation column 61 fractionates hydrocarbon stream 15 (from distillation column 57 via catalytic conversion unit 59) into a contaminant free overhead vapor stream 11 and a contaminant $C_6^+$ liquid, using reboiler 62 and integrated cooling condenser 60. As above, the cooling coil can be installed external to the column complete with reflux drum and pumps (not shown), but can also be chilled with refrigeration. The contaminant free overhead vapor stream 11 (which contains the $C_6$ and lighter components) is combined with the treated gas stream 9 from absorber 54 forming stream 12. The combined treated gas typically contains less than 20 ppmv sulfur content. The bottom liquid product 16 of second distillation column 61 contains the organic sulfur and $C_6^+$ components, is cooled in exchanger 63 to form stream 17 that is recycled back to a hydrotreater unit in the hydrocarbon processing unit 64 for further conversion and production of a contaminant free $C_6^+$ hydrocarbon liquid stream 18. Most typically, the hydrocarbon processing unit further includes an amine unit, Claus plant or other configuration that captures the sulfur emission from the hydrotreater unit.

Alternatively, in even more preferred aspects, the absorber is configured to receive two lean oil streams. For example, in one preferred aspect, the absorber may include a top scrubbing stage that employs a second lean oil (which is preferably sulfur free and has a higher molecular weight than the first lean oil) to further reduce the sulfur content of the treated gas from the lower stage. With such additional scrubbing stage, over 99% of the mercaptans and organic sulfurs are removed with the higher molecular weight lean oil which can be recycled back to the refinery's hydrotreating unit, thus eliminating the mercaptan catalytic conversion step.

Figure 3:
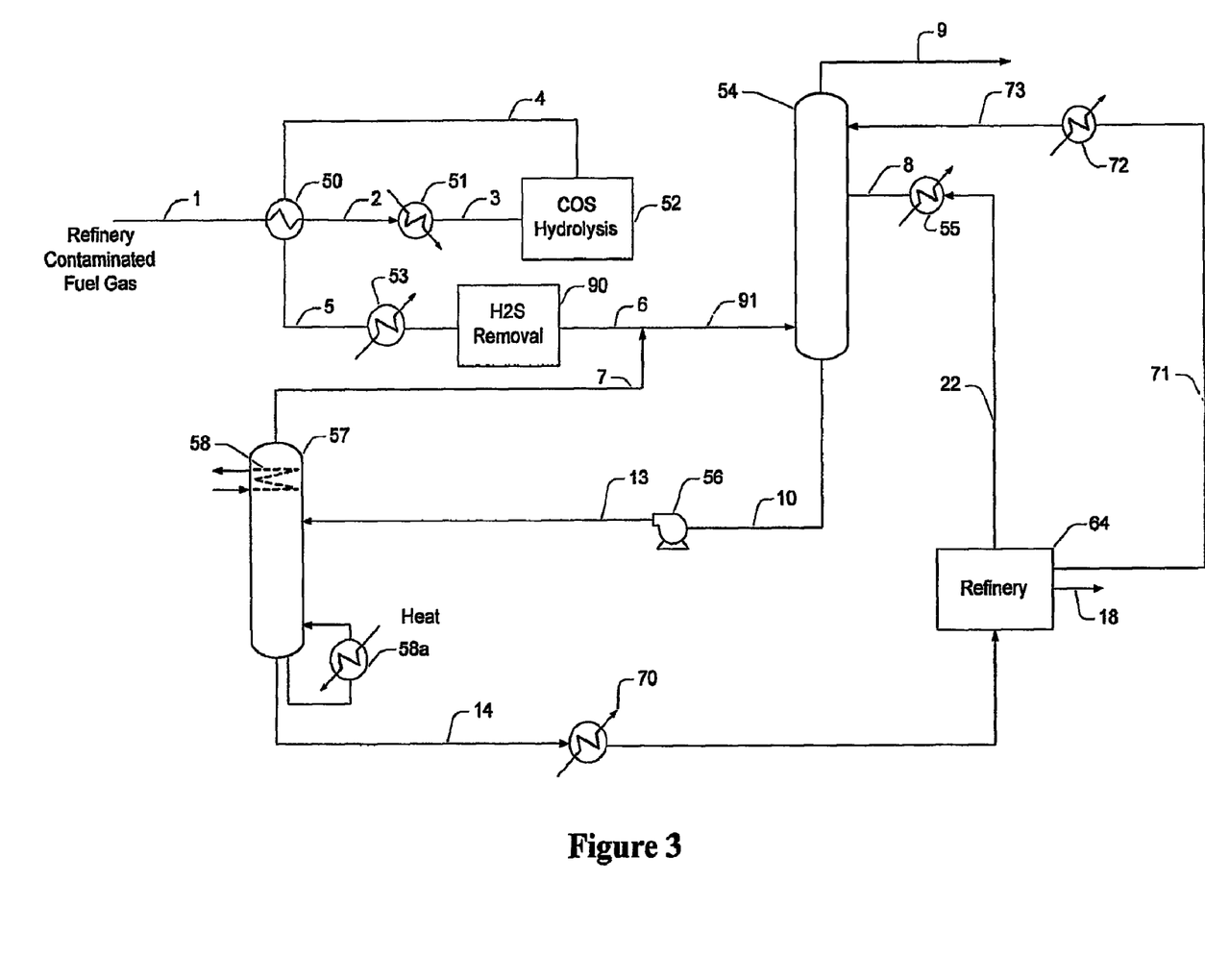
FIG. 3 is an exemplary schematic of another gas treatment plant according to the inventive subject matter.

FIG. 3 exemplarily depicts one such configuration. Here, the top stage of absorber 54 receives a hydrotreated lean oil 73 (preferably with less than 100 ppmw sulfur) and the lower stage receives a lean oil 8, that can be raw naphtha (with less than 0.1 wt % sulfur). The hydrotreated lean oil 73 is preferably a higher boiling point hydrocarbon with higher molecular weight that is suitable for selective complex sulfur absorption. To enhance the absorption efficiency, the lean oils 73 and 8 are cooled with cooling water or refrigeration in coolers 72 and 55, respectively, allowing the lean oil absorber 54 to operate at significantly lower temperatures. Similar to the configuration of FIG. 2 above, the absorber 54 produces a complex, sulfur rich lean oil bottom fluid 10 that is pumped by pump 56 forming stream 13 that is fed to the distillation column 57. Desulfurized gas leaves the absorber as stream 9 for further processing. The distillation column 57 produces a light overhead vapor 7 that is as before recycled back to the absorber via combination with stream 6 from the $H_2S$ removal unit forming stream 91. The complex sulfur rich lean oil bottom product 14 from distillation column 57 is (after being cooled in cooler 70) recycled to a hydrotreater unit in the hydrocarbon processing unit 64, which provides both lean oils as ultra-lean hydrotreated stream 71 and lean stream 22. It should be particularly noted that in this configuration, the catalyst conversion stage and the second distillation column of the single lean oil configuration of FIG. 2 are not required, which significant reduces the overall processing and equipment cost. The remainder of the process in FIG. 3 is substantially identical to that of FIG. 2. Therefore, with respect to like numerals and components, the same considerations for FIG. 2 apply to FIG. 3. Consequently, it should be recognized that the use of two different lean oils significantly increases absorption efficiency, and substantially reduces the consumption of hydrotreated lean oil.

Figure 4:
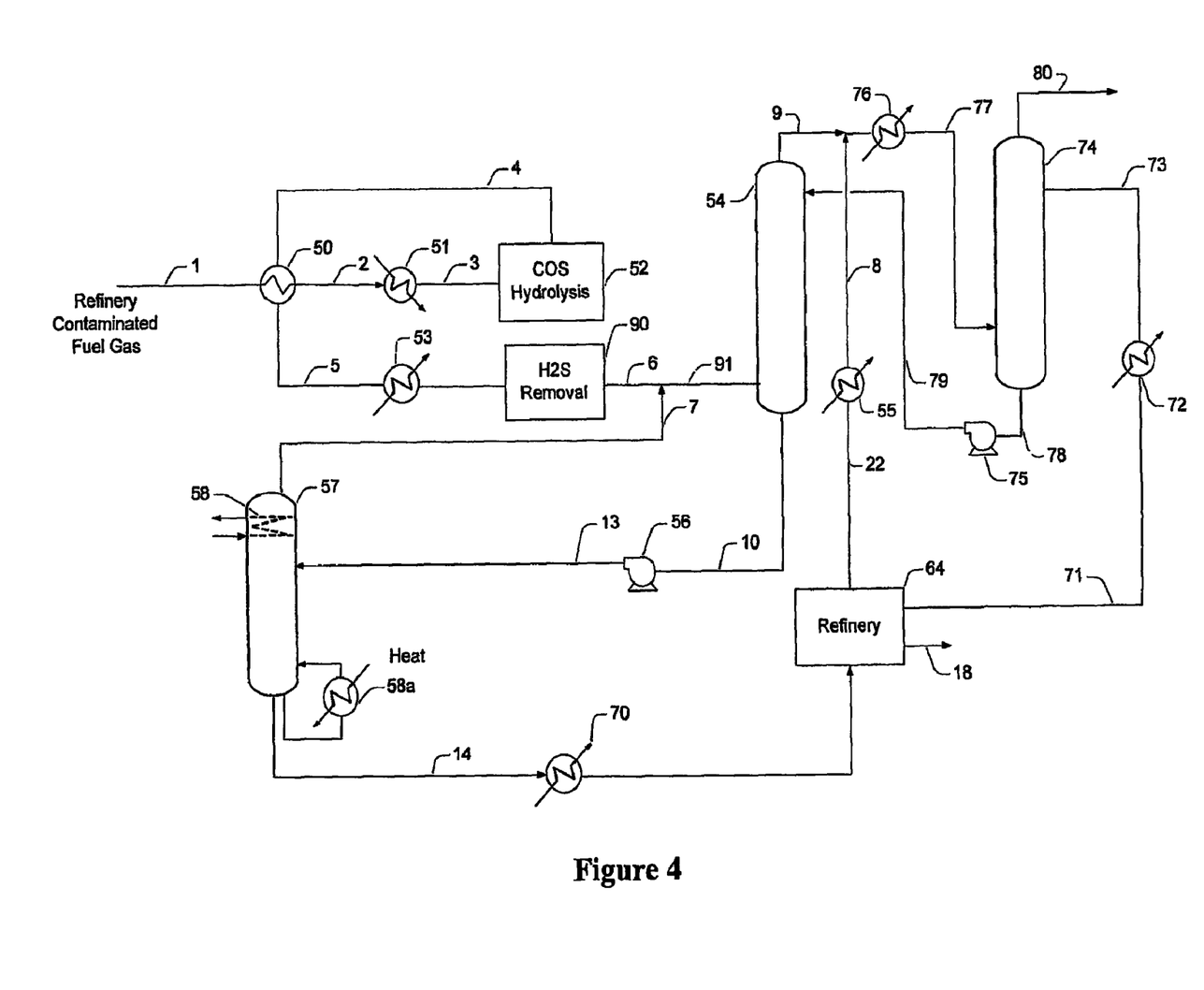
FIG. 4 is an exemplary schematic of a further gas treatment plant according to the inventive subject matter.

In another especially preferred aspect as exemplarily shown in FIG. 4, an upstream absorber is included that receives the feed gas from the COS hydrolysis and/or $H_2S$ removal unit to produce an overhead vapor that is combined with the first lean oil stream prior to entering the downstream absorber. The downstream absorber also receives the second lean oil stream to produce the desulfurized feed gas and a mercaptan enriched hydrocarbon fluid that is fed to the upstream absorber. Most preferably, the overhead vapor from the upstream absorber is cooled by an intercooler prior to entry into the downstream absorber. It should be noted that contemplated configurations and methods significantly reduce, if not even almost completely eliminate emission of most sulfurous components, hydrocarbons, and other contaminants while providing a sulfur and contaminant-depleted gas that meets stringent environmental standards.

With further reference to FIG. 4, absorber 74 is located downstream of absorber 54. It is further preferred that intercooler 76 cools the treated gas from the upstream absorber 54 by removing the heat of absorption to thus increase the sulfur absorption efficiency in the downstream absorber 74. In this configuration, the overhead vapor stream 9 from the first absorber is mixed with the unhydrotreated lean oil stream 8 (previously cooled in cooler 55 from stream 22 with sulfur content of less than about 0.1 w %) and is cooled in exchanger 76 to about 90° F. or lower. The so formed two-phase mixed stream 77 is flashed into the bottom of the downstream absorber 74. The flashed vapor ascends in the column while being scrubbed with hydrotreated lean oil stream 73 (with less than 100 ppmw sulfur) which is cooled in cooler 72 prior to entry into the downstream absorber. With this second stage scrubbing, residual unhydrotreated lean oil is absorbed by the hydrotreated lean oil, producing a treated gas 80 that is almost entirely sulfur free. The mercaptan-enriched semi-lean oil 78 from the downstream absorber (which is a mixture of the hydrotreated and the unhydrotreated lean oil), is pumped by pump 75 forming stream 79 and is fed to the upstream absorber 54 for further sulfur absorption. The remainder of the process in FIG. 4 is substantially identical to that of FIG. 3. Therefore, with respect to like numerals and components, the same considerations of FIG. 3 apply to FIG. 4.

Figure 5:
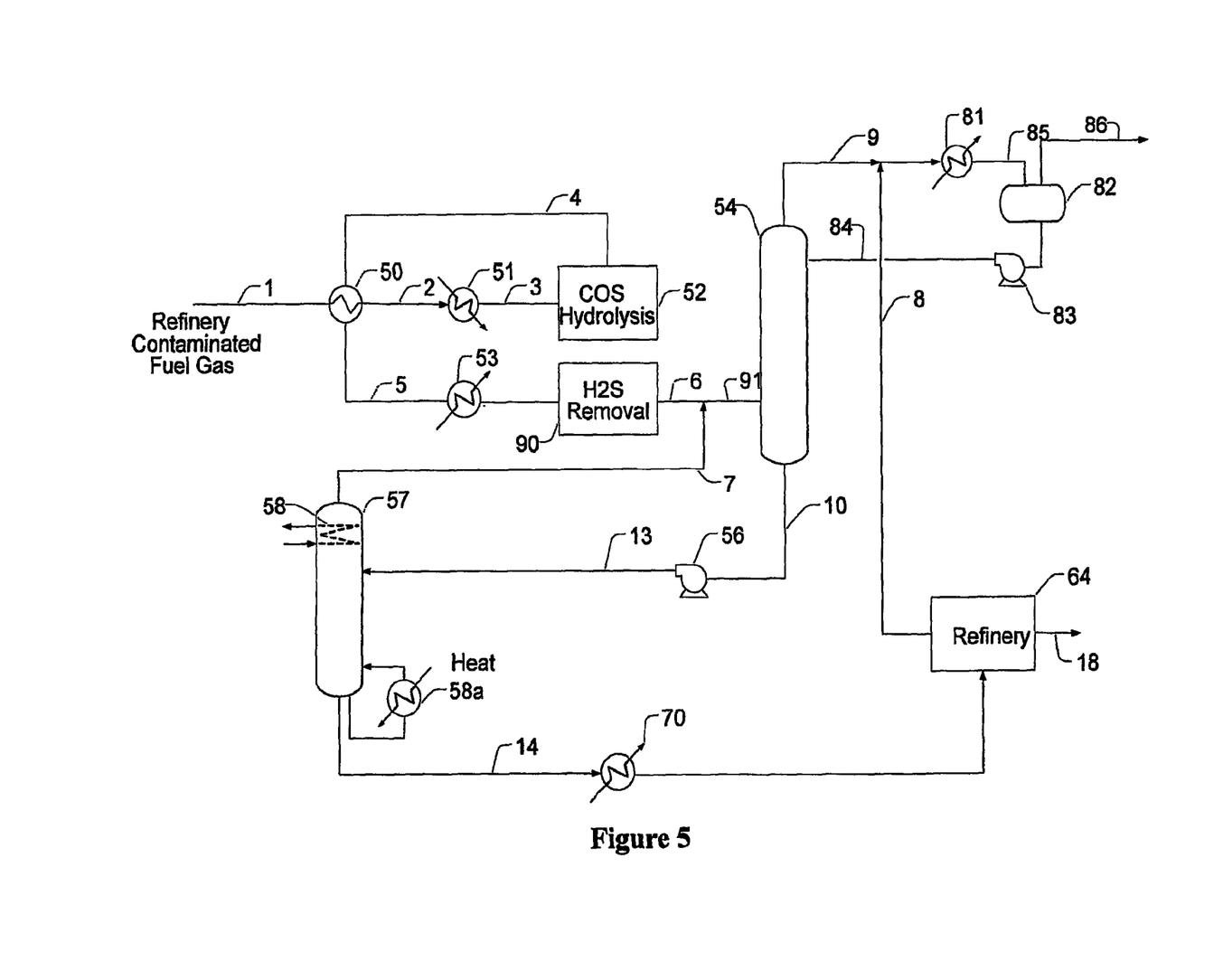
FIG. 5 is an exemplary schematic of yet another gas treatment plant according to the inventive subject matter.

In still further contemplated alternative aspects, an overhead cooling system may be employed with the absorber in which condensed absorber overhead product is used as the first lean oil and in which hydrotreated lean oil is used as the second lean oil that is combined with the overhead product prior to condensation. Such configuration further reduces sulfur content in the treated gas. One such exemplary configuration is shown in FIG. 5, where an overhead chilling system is used to cool the treated gas to an even lower temperature to thereby enhance the lean oil absorption process. Here, the lean oil 8 is preferably mixed with treated gas 9 from the first absorber, and the mixture is cooled in cooler 81 that removes the heat of absorption. The two phase stream 85 is separated in separator 82, producing a sulfur free overhead gas 86 and a semi-lean oil that is pumped by pump 83 to stream 84 that is fed to the absorber 54. With a sufficiently low temperature, the use of a second absorber as shown above is not required. It should be noted that the low overhead temperature is limited by the hydrate formation temperature and may therefore require gas dehydration or a hydrate inhibition/prevention process. Once more, with respect to like numerals and components, the same considerations of FIG. 3 apply to FIG. 5. Additionally contemplated aspects and considerations related to feed gas treatment according to the inventive subject matter are disclosed in our copending International application with the serial number PCT/US07/02097, which is incorporated by reference herein.

In another contemplated alternative aspect, contemplated processes may further include a hydrotreater configuration that uses a recycle lean oil for temperature control, thus permitting saturation of the olefinic hydrocarbons and simultaneous conversion of the residual mercaptans avoiding hydrocarbon cracking and gums formation. Saturation of the olefinic hydrocarbons is a necessary step to minimize NOx formation in gas turbines in power plant.

Figure 6:
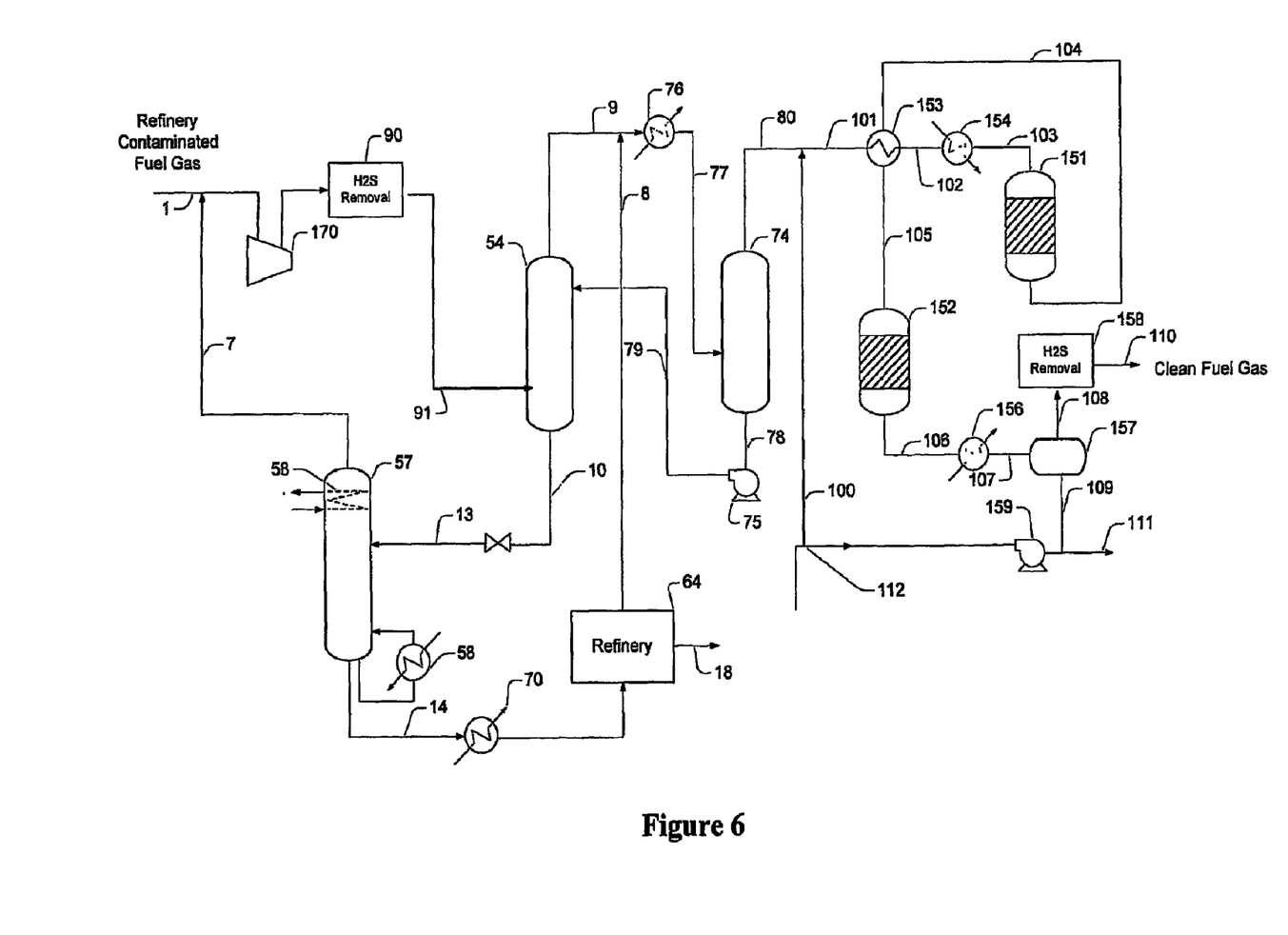
FIG. 6 is an exemplary schematic of yet a further gas treatment plant according to the inventive subject matter.

One such exemplary configuration is shown in FIG. 6, where an upstream treating and contaminant removal is used in a manner similar as described above and that may further include a feed gas compressor 170. The treated gas stream 80 from the downstream absorber 74 is mixed with lean oil 100 forming 101 and is heated in a feed/effluent exchanger 153. A second heater 154, typically using high pressure steam, is used to heat up the two phase mixture to about 450° F. forming stream 103. In hydrotreater reactor 151, olefinic hydrocarbons are converted to paraffinic hydrocarbons and the sulfur contaminants (mainly mercaptans) are converted to $H_2S$. Typically, cobalt molybdenum or nickel molybdenum based catalysts are used to promote the olefinic saturation reaction and the desulfurization reaction which are highly exothermic reactions. If uncontrolled, the extreme high temperature will produce side reactions that typically form carbon deposits or gums. To avoid gum formation that will cause fouling of the heat exchangers and reactor, temperature rise in the hydrotreater reactor is controlled at less than 50° F. to 100° F. temperature by evaporating the lean content in stream 103. The reactor effluent 104 is then heat exchanged with the feed gas 101 forming the effluent stream 105 which is further processed in COS hydrolysis reactor 152 where the COS formed in the hydrotreater is re-converted back to $H_2S$. The COS hydrolysis reactor effluent 106 is cooled with ambient cooler 156 forming stream 107. The vaporized lean oil is recondensed and separated in separator 157 which produces the $H_2S$ containing hydrocarbon stream 108 and the lean oil stream 109. A portion of the lean oil is removed (stream 111) and the remaining portion is recycled by pump 159 to the front section of the hydrotreater. Lean oil stream 112 is made up to the unit as needed. The treated gas stream 108 is treated in the $H_2S$ removal unit 158 typically using amine, forming the clean gas stream 110. With respect to like numerals and components, the same considerations of FIG. 4 apply to FIG. 6.

Thus, specific embodiments and applications of configurations and methods for removal of sulfur-containing contaminants from various gases have been disclosed. It should be apparent, however, to those skilled in the art that many more modifications besides those already described are possible without departing from the inventive concepts herein. The inventive subject matter, therefore, is not to be restricted except in the spirit of the present disclosure. Moreover, in interpreting the specification and contemplated claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A gas treatment plant comprising:
 a COS hydrolysis unit configured to hydrolyze COS in a mercaptan-containing feed gas to form a treated feed gas;
 an absorber fluidly coupled to the COS hydrolysis unit and further fluidly coupled to a first and a second conduit that are configured to provide a first and a second lean hydrocarbon fluid to the absorber;
 wherein the absorber is configured to allow contacting of the treated feed gas with the first and a second lean hydrocarbon fluid to thereby produce a mercaptan enriched hydrocarbon fluid and a desulfurized product gas;
 a distillation column coupled to the absorber and configured to receive the mercaptan enriched hydrocarbon fluid and further configured to produce a light overhead vapor and a sulfur rich bottom product; and
 a hydrocarbon processing unit comprising a hydrotreater, wherein the hydrocarbon processing unit is fluidly coupled to the distillation column and configured to receive the sulfur rich bottom product and to produce a sulfur-containing product and at least one of the first and second lean hydrocarbon fluid.

2. The plant of claim 1 further comprising an $H_2S$ removal unit fluidly coupled to the COS hydrolysis unit and configured to remove $H_2S$ from the treated feed gas prior to feeding the treated feed gas into the absorber.

3. The plant of claim 1 further comprising a conduit that is configured to feed the light overhead product to the treated feed gas.

4. The plant of claim 1 wherein the hydrocarbon processing unit is configured to produce the first and the second lean hydrocarbon fluid.

5. The plant of claim 4 further comprising first and second coolers that are configured to cool the first and the second lean hydrocarbon fluid.

6. The plant of claim 4 further comprising a second absorber that is fluidly and upstream coupled to the absorber, wherein the second absorber is configured to receive the treated feed gas and to produce an overhead gas and a second mercaptan enriched hydrocarbon fluid, and wherein the second absorber is further configured to provide the overhead gas to the absorber.

7. The plant of claim 6 wherein the first conduit is configured to provide the first lean hydrocarbon fluid to the overhead gas prior to entering the absorber.

8. The plant of claim 1 further comprising an absorber overhead condenser and reflux drum configured to produce a reflux to the absorber as the first lean hydrocarbon fluid via the first conduit, wherein the second conduit is configured to combine the desulfurized product gas with the second lean hydrocarbon fluid in a location upstream of the reflux drum, and wherein the overhead condenser is optionally configured to cool the first and second lean hydrocarbon fluids.

9. The plant of claim 1 wherein the treated gas is further processed in a hydrotreater and COS hydrolysis reactor for saturation of the olefinic hydrocarbons and conversion of the residual mercaptans using a recycled lean oil to control the reactor temperatures sufficiently to eliminate fouling.

10. The plant of claim 1 wherein the distillation column and the hydrocarbon processing unit are fluidly coupled to each other such that the sulfur rich bottom product is fed to the hydrocarbon processing unit without passing through a catalytic oxidation unit.

11. A method of removing sulfur compounds from a feed gas, comprising:
hydrolyzing COS in a sulfur and mercaptan-containing feed gas to form a treated feed gas;
absorbing sulfur species from the treated feed gas in an absorber using a first and a second lean hydrocarbon fluid to thereby produce a mercaptan enriched fluid and a desulfurized product gas;
separating the mercaptan enriched fluid in a distillation column to produce a light overhead vapor and a sulfur rich bottom product; and
processing the sulfur rich bottom product in a hydrocarbon processing unit that has a hydrotreater to produce a sulfur-containing product and at least one of the first and second lean hydrocarbon fluid.

12. The method of claim 11 further comprising a step of removing $H_2S$ in an $H_2S$ removal unit prior to feeding the treated feed gas into the absorber.

13. The method of claim 11 further comprising a step of feeding the light overhead vapor to the treated feed gas.

14. The method of claim 11 wherein the hydrocarbon processing unit that has the hydrotreater produces the first and second lean hydrocarbon fluid.

15. The method of claim 14 further comprising a step of cooling the first and the second lean hydrocarbon fluid.

16. The method of claim 14 further comprising a step of providing a second absorber that is fluidly and upstream coupled to the absorber, wherein the second absorber receives the treated feed gas and produces an overhead gas and a second mercaptan enriched hydrocarbon fluid, and wherein the second absorber provides the overhead gas to the absorber.

17. The method of claim 16 wherein the first lean hydrocarbon fluid is combined with the overhead gas prior to entering the absorber.

18. The method of claim 11 further comprising providing an absorber overhead condenser and reflux drum to produce a reflux to the absorber as the first lean hydrocarbon fluid, and combining the desulfurized product gas with the second lean hydrocarbon fluid in a location upstream of the reflux drum.

19. The method of claim 18 wherein the absorber overhead condenser cools the first and second lean hydrocarbon fluids.

20. The method of claim 11 wherein the sulfur rich bottom product is fed to the processing unit without passing through a catalytic oxidation unit.

* * * * *